United States Patent
Craig et al.

(10) Patent No.: US 7,291,740 B2
(45) Date of Patent: Nov. 6, 2007

(54) 5-[4-[2-(N-METHYL-N-(2-PYRIDYL)AMINO)-ETHOXY]BENZYL]THIAZOLIDINE-2,4-DIONE MESYLATE SALT

(75) Inventors: Andrew Simon Craig, Tonbridge (GB); Tim Chien Ting Ho, Tonbridge (GB); Michael Millan, Tonbridge (GB); Deirdre O'Keeffe, Tonbridge (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

(21) Appl. No.: 11/199,779

(22) Filed: Aug. 9, 2005

(65) Prior Publication Data

US 2006/0040993 A1 Feb. 23, 2006

Related U.S. Application Data

(63) Continuation of application No. 10/451,215, filed as application No. PCT/GB01/05751 on Dec. 21, 2001, now abandoned.

(30) Foreign Application Priority Data

| Dec. 22, 2000 | (GB) | ................................ 0031521.8 |
| Dec. 22, 2000 | (GB) | ................................ 0031524.2 |
| Dec. 22, 2000 | (GB) | ................................ 0031526.7 |
| Dec. 22, 2000 | (GB) | ................................ 0031528.3 |

(51) Int. Cl.
*C07D 417/10* (2006.01)

(52) U.S. Cl. ................................ 546/269.7

(58) Field of Classification Search ............ 546/269.7; 514/342

See application file for complete search history.

(56) References Cited

U.S. PATENT DOCUMENTS 5,741,803 A 4/1998 Pool et al. ................ 514/342
5,910,592 A 6/1999 Pool et al. ................ 546/269.7

FOREIGN PATENT DOCUMENTS

EP 0 306 228 3/1989
WO WO 94/05659 3/1994

OTHER PUBLICATIONS

Brittain et al., "Polymorphism in Pharmaceutical Solids", NY:Marcel Dekker, Inc., 1999, pp. 1-2, 185.*
Muzaffar et al., "Polymorphism and Drug Availability", J of Pharmacy (Lahore) (1979), 1(1), pp. 59-66.*
Taday et al., "Using Terahertz Pulse, etc.," J of Pharmaceutical Sciences, 92(4), 2003, pp. 831-838.*
Wall et al., "Pharmaceutical Applications, etc.," Pharmaceutical Manufacturing, 3(2), 1986, pp. 32-34.*
Jain et al., "Polymorphism in Pharmacy" Indian Drugs, 1986, 23(6), pp. 315-329.*
Otsuka et al., "Effect of Polymorphic Forms, etc.," Chem. Pharm. Bull. 47(6), 1999, pp. 852-856.*
Doelker et al. CA 132:325872, 2000.*
Ulicky et al., "Comprehensive Dictionary of Physical Chemistry", NY: PTR Prenctice Hall 1992, p. 21.*
Brittain et al. Polymorphism in Pharmaceutical Solids, NY: Mercel Dekker, Inc. 1999, pp. 228-330.
Chemical & Engineering News, Feb. 2003, pp. 32-35.
Concise Encyclopedia Chemistry, pp. 872-873 (1993).
Haleblian et al., J. Pharm. Sci., 58: 911-929 (1969).
US Pharmacopia, pp. 1843-1844 (1995).

* cited by examiner

*Primary Examiner*—Patricia L. Morris
(74) *Attorney, Agent, or Firm*—Kathryn L. Sieburth; Mary E. McCarthy; Charles M. Kinzig

(57) ABSTRACT

Disclosed are 5-[4-[2-(N-Methyl-N-(2-pyridyl)amino)ethoxy]benzyl]thiazolidine-2,4-dione mesylate salts, or solvates thereof; processes for preparing such compounds, compositions comprising such compounds and the use of such compounds in medicine.

3 Claims, 13 Drawing Sheets

Figure 1 Infrared spectrum of the Mesylate Form I
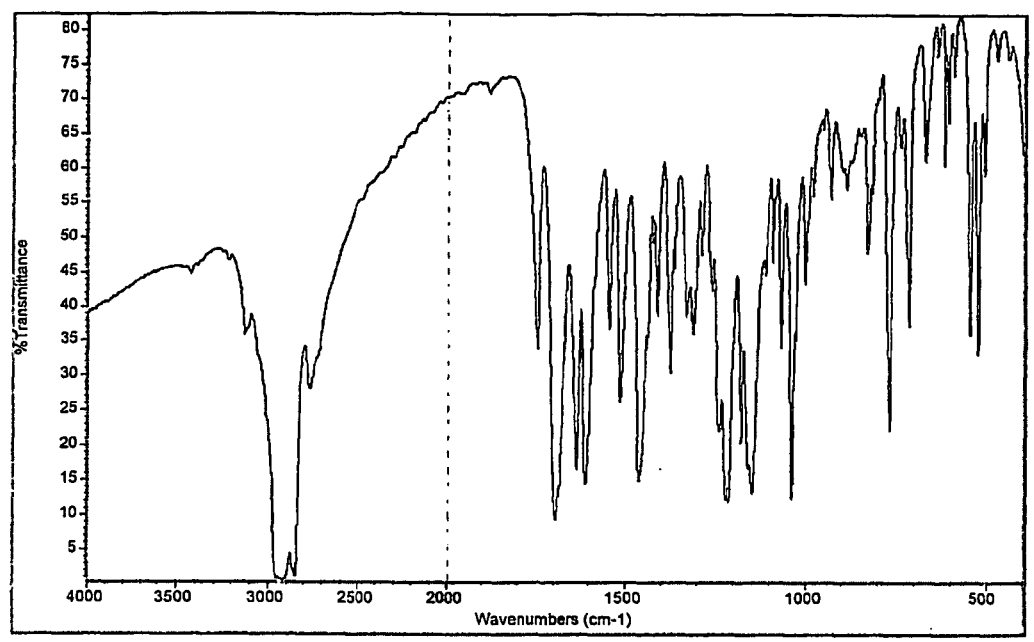

Figure 2 Raman spectrum of the Mesylate Form I
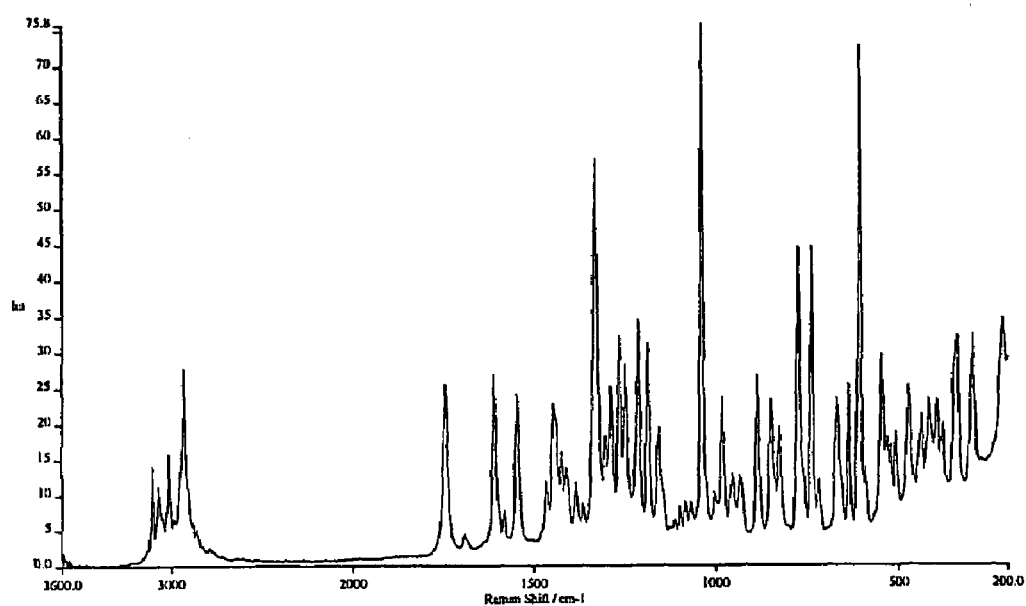

Figure 3    X-Ray Powder Diffractogram for the Mesylate Form I
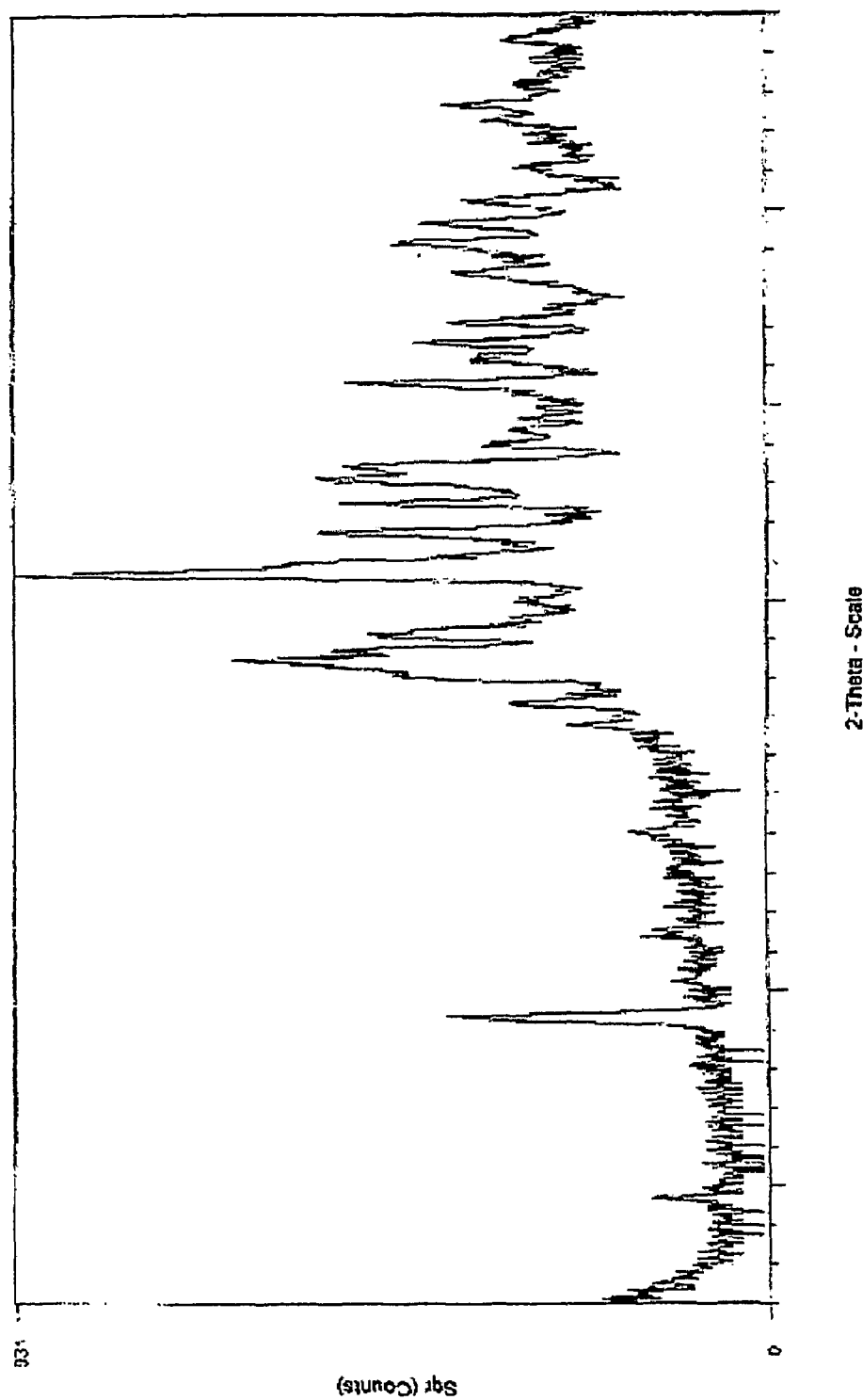

Figure 4    Infrared spectrum of the Mesylate Form II
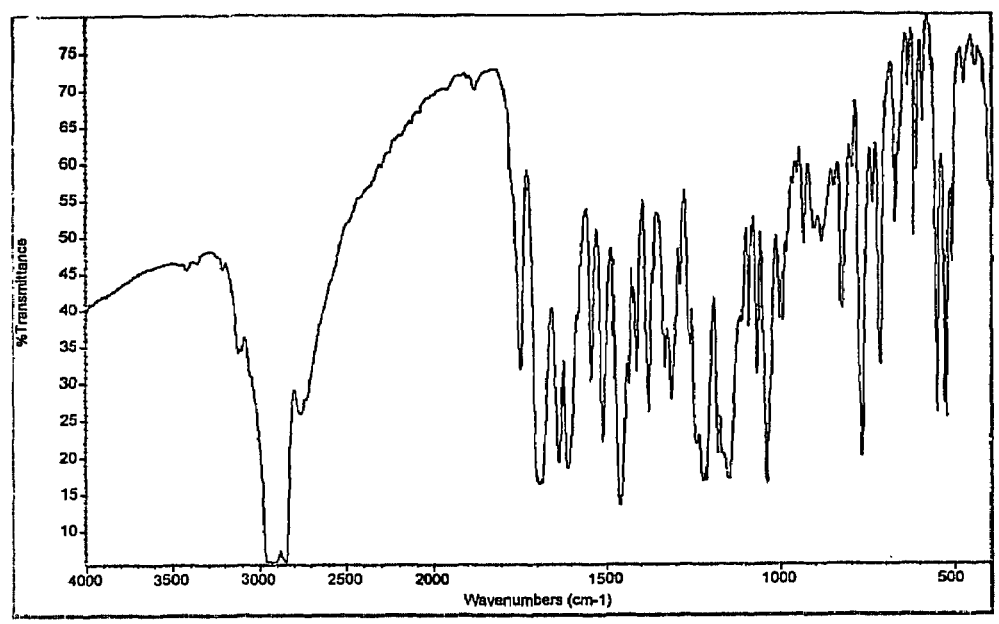

Figure 5 Raman spectrum of the Mesylate Form II
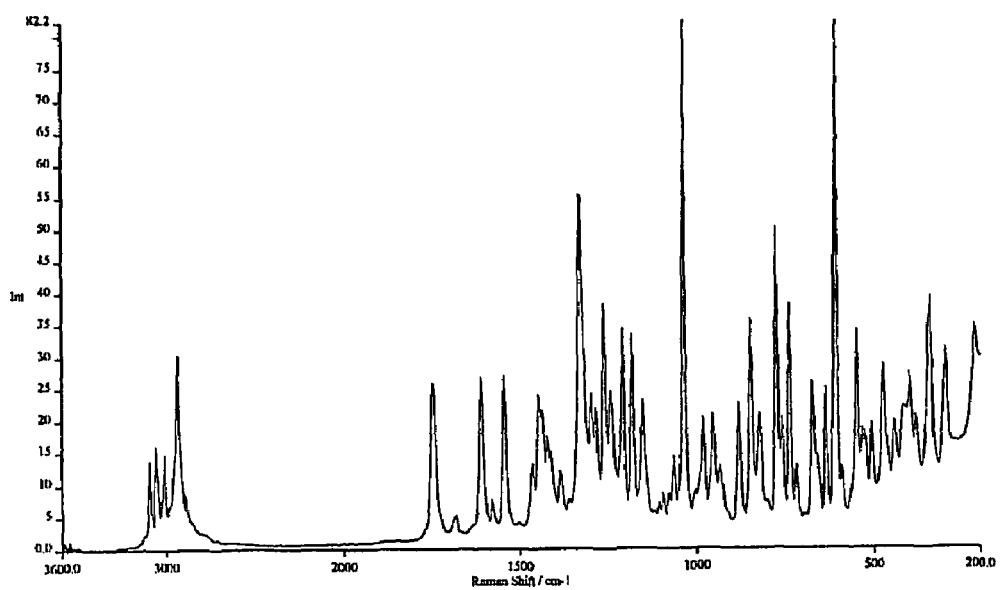

Figure 6 X-Ray Powder Diffractogram for the Mesylate Form II
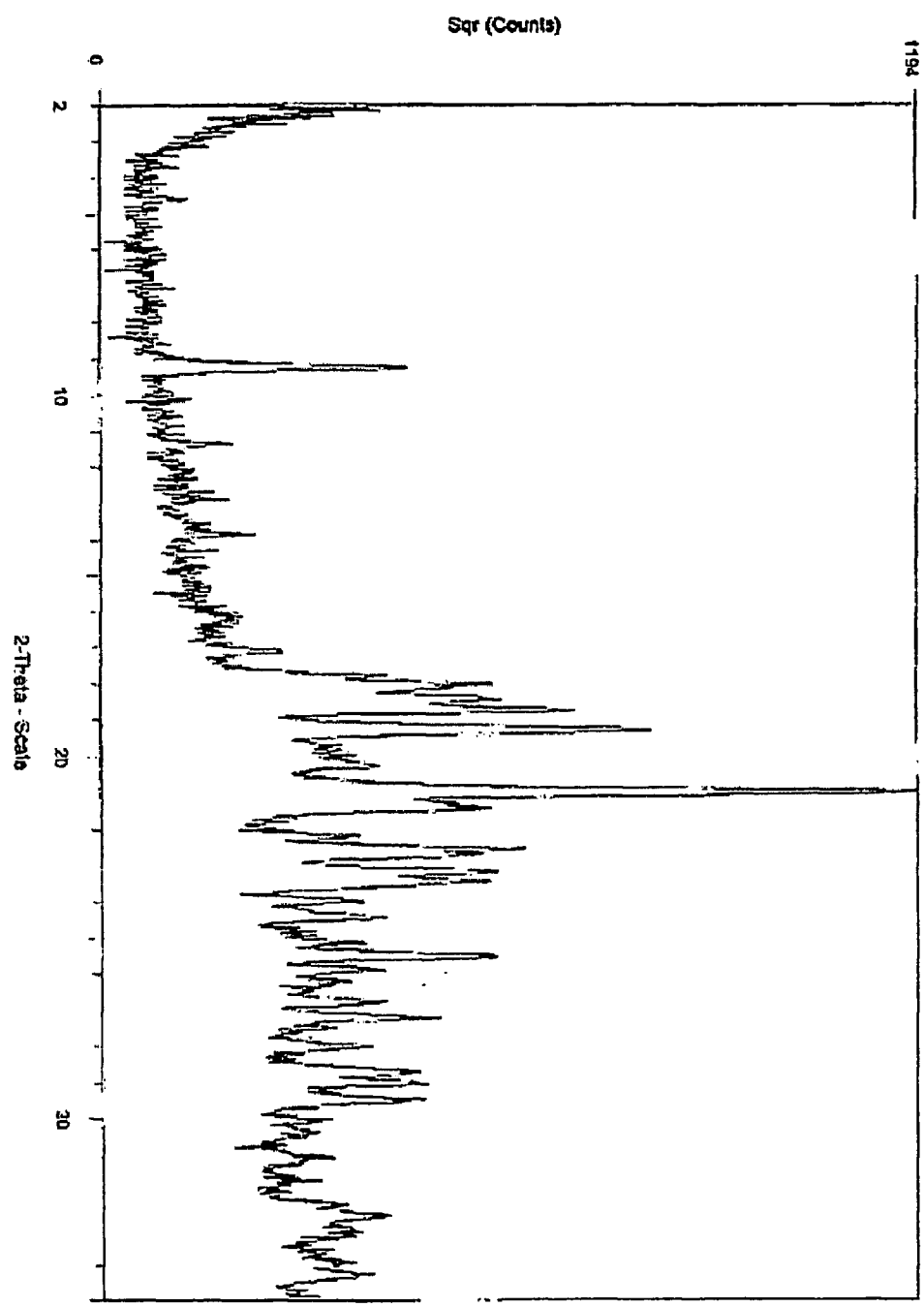

Figure 7    Infrared spectrum of the Mesylate Form III
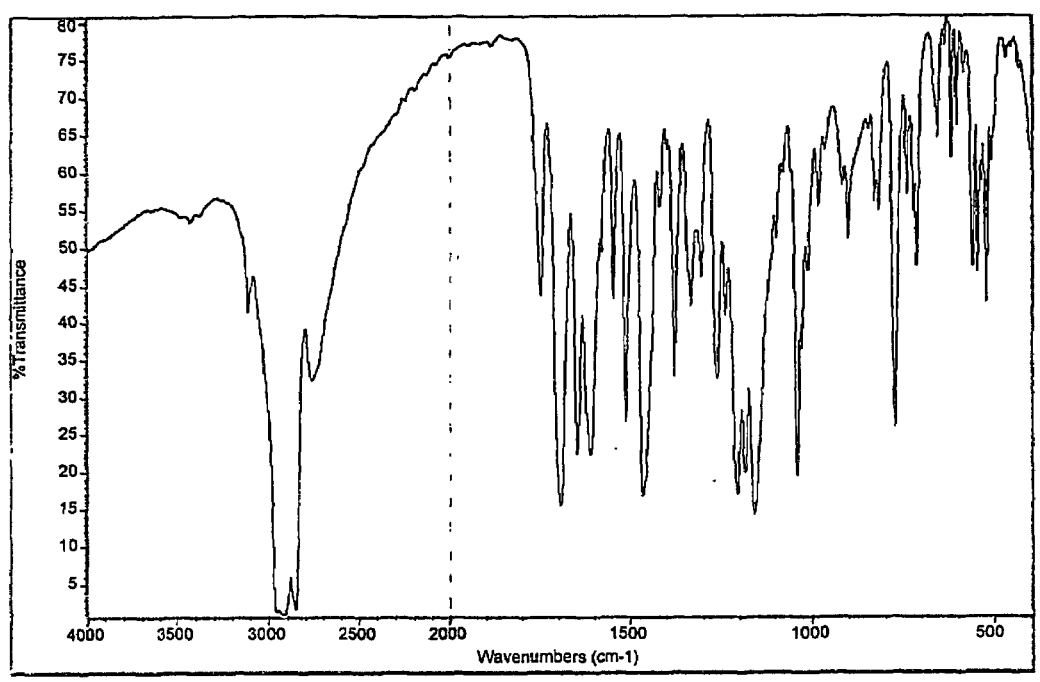

Figure 8    Raman spectrum of the Mesylate Form III
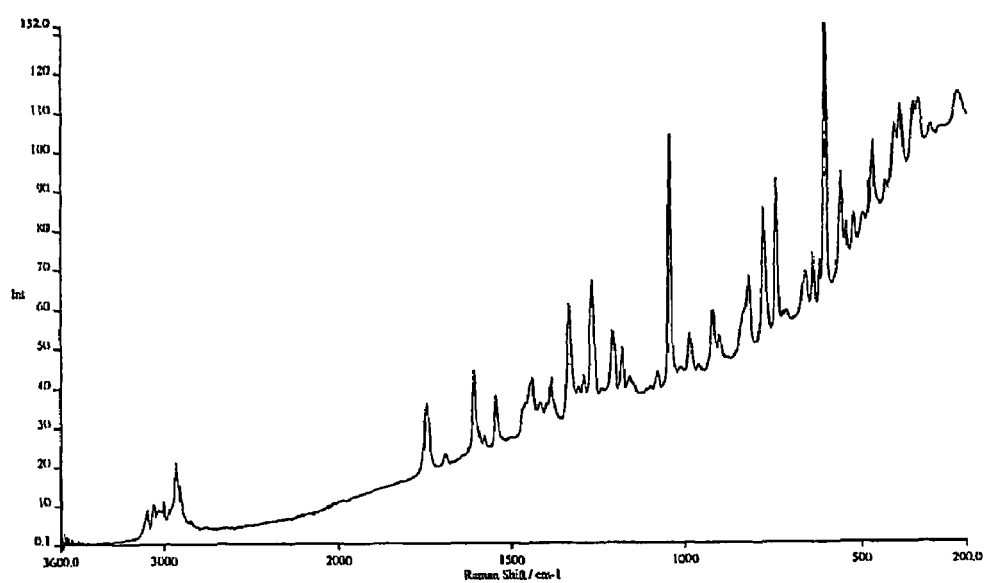

Figure 9    X-Ray Powder Diffractogram for the Mesylate Form III
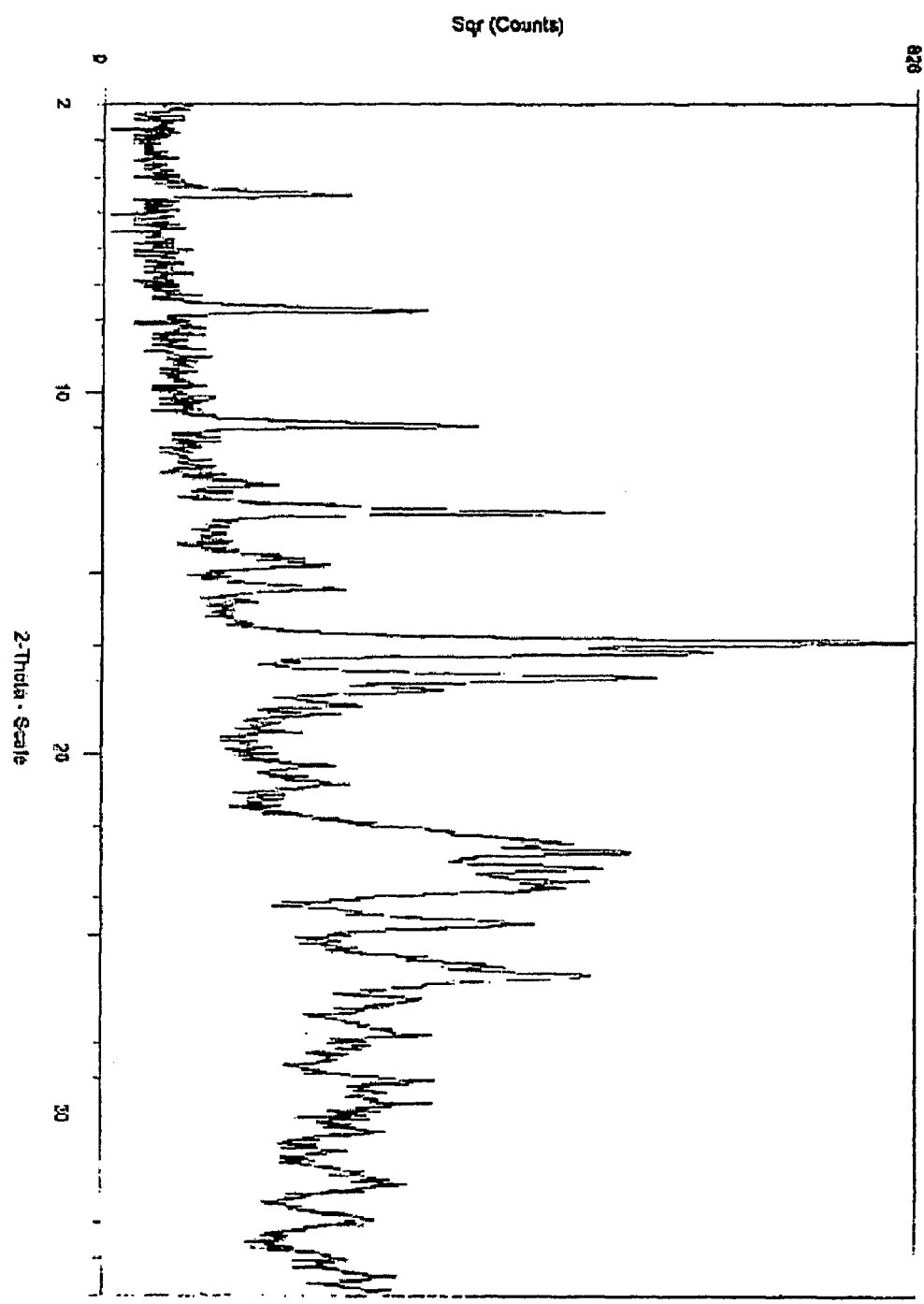

Figure 10   Infrared spectrum of the Mesylate Form IV
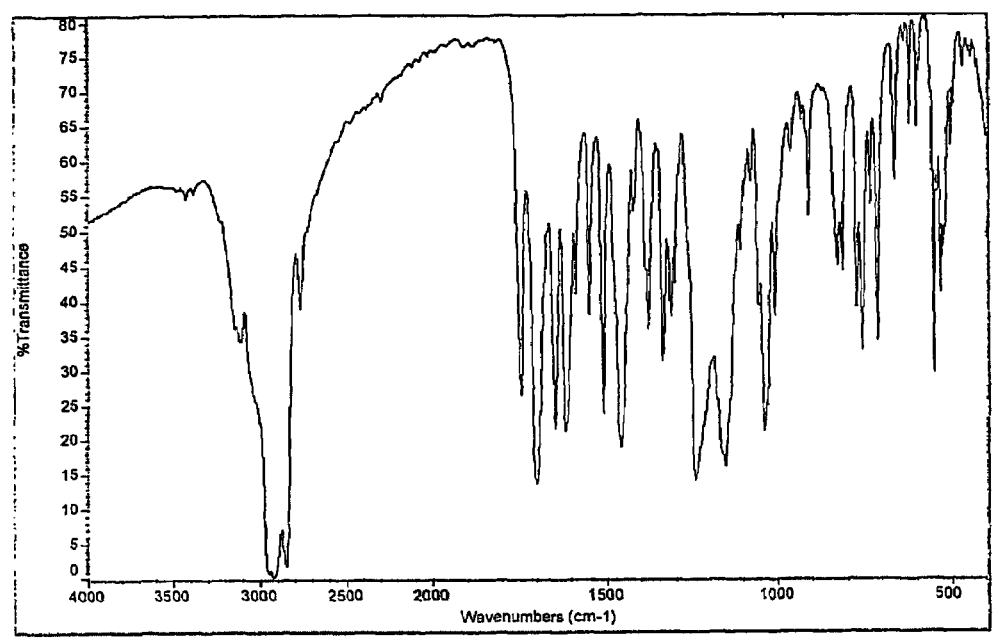

Figure 11   Raman spectrum of the Mesylate Form IV
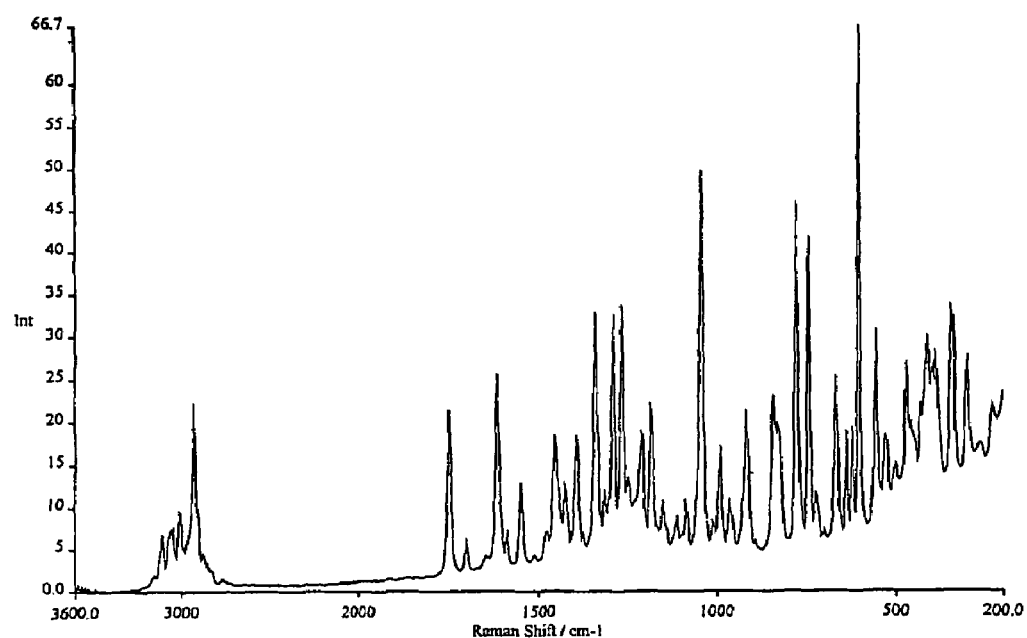

Figure 12    X-Ray Powder Diffractogram for the Mesylate Form IV
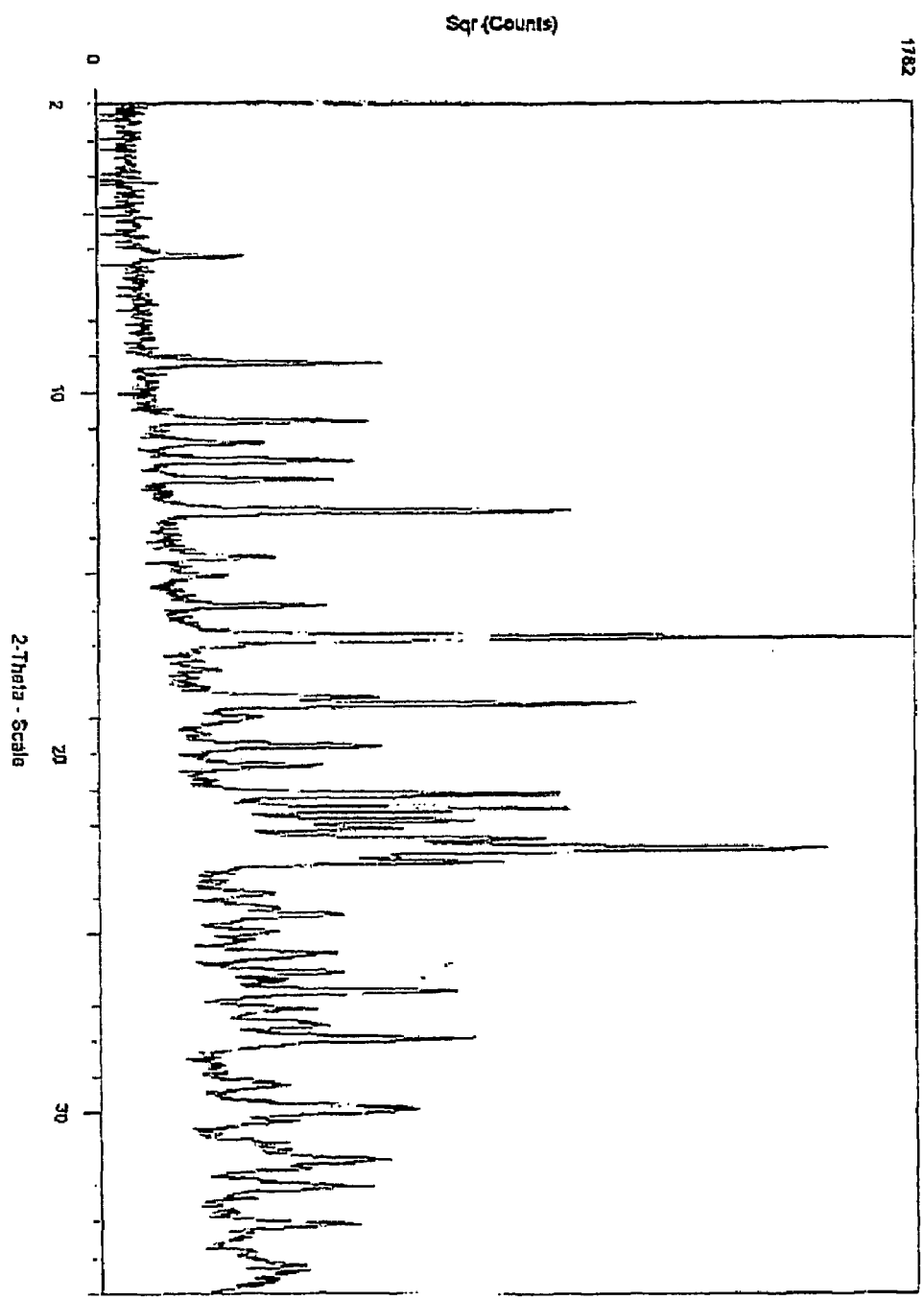

Figure 13    Solid State 13C NMR spectrum of the Mesylate Form IV
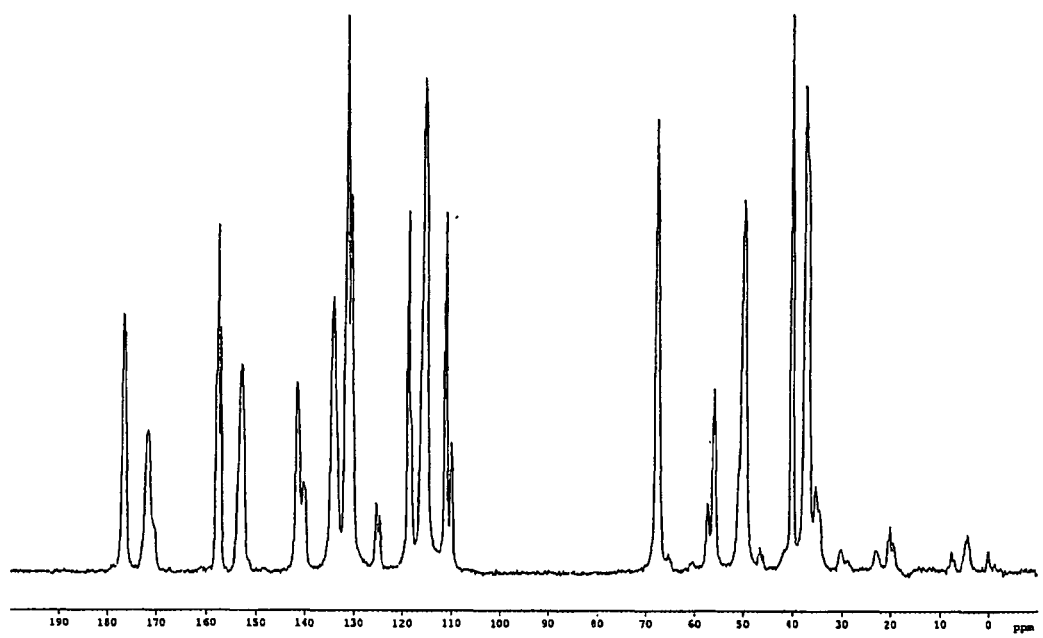

5-[4-[2-(N-METHYL-N-(2-PYRIDYL)AMINO)-ETHOXY]BENZYL]THIAZOLIDINE-2,4-DIONE MESYLATE SALT

This application is a continuation of U.S. patent application Ser. No. 10/451,215, filed Dec. 4, 2003 (now abandoned), which is a 371 of International Application No. PCT/GB01/05751, filed Dec. 21, 2001.

This invention relates to a novel pharmaceutical, to a process for the preparation of the pharmaceutical and to the use of the pharmaceutical in medicine.

BRIEF DESCRIPTION OF THE DRAWINGS

FIG. 1 is the infrared spectrum of Mesylate Form I, as taken in a mineral oil dispersion.

FIG. 2 is the Raman spectrum of Mesylate Form I.

FIG. 3 is the X-ray powder diffractogram of Mesylate Form I.

FIG. 4 is the infrared spectrum of Mesylate Form II, as taken in a mineral oil dispersion.

FIG. 5 is the Raman spectrum of Mesylate Form II.

FIG. 6 is the X-ray powder diffractogram of Mesylate Form II.

FIG. 7 is the infrared spectrum of Mesylate Form III, as taken in a mineral oil dispersion.

FIG. 8 is the Raman spectrum of Mesylate Form III.

FIG. 9 is the X-ray powder diffractogram of Mesylate Form III.

FIG. 10 is the infrared spectrum of Mesylate Form IV, as taken in a mineral oil dispersion.

FIG. 11 is the Raman spectrum of Mesylate Form IV.

FIG. 12 is the X-ray powder diffractogram of Mesylate Form IV.

FIG. 13 is the solid state $^{13}$C NMR spectrum of Mesylate Form IV.

EP-A-0 306 228 relates to certain thiazolidinedione derivatives disclosed as having hypoglycaemic and hypolipidaemic activity. The compound of Example 30 of EP-A-0 306 228 is 5-[4-[2-(N-methyl-N-(2-pyridyl)amino)ethoxy]benzyl]thiazolidine-2,4-dione (hereinafter referred to as "Compound (I)").

WO 94/05659 discloses certain salts of the compounds of EP-A-0 306 228. The preferred salt of WO 94/05659 is the maleic acid salt. Methanesulfonic acid is mentioned as a potential counter-ion but the preparation of a methanesulfonic acid salt is not exemplified.

We have now prepared and characterised a methanesulfonate salt of Compound (I) and discovered that a novel form of methanesulfonate salt (hereinafter also referred to as the "Mesylate") is formed that is particularly stable and hence is suitable for bulk preparation and handling. The Mesylate also has a high melting point, shows particularly good aqueous solubility and possesses good bulk flow properties. The Mesylate is therefore surprisingly amenable to large scale pharmaceutical processing and especially to large scale milling.

The novel salt can be prepared by an efficient and economic process particularly suited to large-scale preparation.

The novel Mesylate also has useful pharmaceutical properties and in particular it is indicated to be useful for the treatment and/or prophylaxis of diabetes mellitus, conditions associated with diabetes mellitus and certain complications thereof.

Accordingly, the present invention provides 5-[4-[2-(N-methyl-N-(2-pyridyl)amino)ethoxy]benzyl]thiazolidine-2, 4-dione mesylate salt, or solvate thereof.

It has been found that the Mesylate exists in more than one novel polymorphic form. The present invention extends to all such forms whether in a pure polymorphic form or when admixed with any other material, such as another polymorphic form. Herein, the novel polymorpic forms of the Mesylate are referred to as Form I, Form II, Form III and Form IV. Each of the said forms may also be referred to herein as the Mesylate as appropriate.

Suitably, the invention provides the Mesylate, or a solvate thereof, suitably as characterised by data provided by at least one of the following: infrared, Raman, X-ray powder diffraction or nuclear magnetic resonance and melting point data as provided herein, including partial spectral data provided herein In a further aspect the invention provides Mesylate Form I, or solvate thereof.

In a further aspect the invention provides Mesylate Form II, or solvate thereof.

In a further aspect the invention provides Mesylate Form III, or solvate thereof.

In a preferred aspect the invention provides Mesylate Form IV, or solvate thereof.

In a particular aspect, the present invention provides 5-[4-[2-(N-methyl-N-(2-pyridyl)amino)ethoxy]benzyl]thiazolidine-2,4-dione mesylate salt (Form I), characterised by (i) an infrared spectrum containing peaks at about 1515, 670, 606 cm$^{-1}$; and/or (ii) a Raman spectrum containing peaks at about 887, 671 cm$^{-1}$; and/or (iii) an X-ray powder diffraction (XRPD) pattern containing peaks at about 17.4, 19.6, 20.0, 28.5 °2θ.

Depending on the solvent from which the Mesylate is recovered, the Mesylate may be obtained as a solvate, and such solvate is a favoured aspect of the invention.

In one favoured aspect, the Mesylate provides an infrared spectrum substantially in accordance with FIG. 1.

In one favoured aspect, the Mesylate provides a Raman spectrum substantially in accordance with FIG. 2.

In one favoured aspect, the Mesylate provides an X-Ray powder diffraction pattern (XRPD) substantially in accordance with Table 1 or FIG. 3.

In a particular aspect, the present invention provides 5-[4-[2-(N-methyl-N-(2-pyridyl)amino)ethoxy]benzyl]thiazolidine-2,4-dione mesylate salt (Form II), characterised by (i) an infrared spectrum containing peaks at about 674, 609 cm$^{-1}$; and/or (ii) a Raman spectrum containing peaks at about 883, 609 cm$^{-1}$; and/or (iii) an X-ray powder diffraction (XRPD) pattern containing peaks at about 20.2, 28.0, 28.8, 29.5 °2θ.

Depending on the solvent from which the Mesylate is recovered, the Mesylate may be obtained as a solvate, and such solvate is a favoured aspect of the invention.

In one favoured aspect, the Mesylate provides an infrared spectrum substantially in accordance with FIG. 4.

In one favoured aspect, the Mesylate provides a Raman spectrum substantially in accordance with FIG. 5.

In one favoured aspect, the Mesylate provides an X-Ray powder diffraction pattern (XRPD) substantially in accordance with Table 2 or FIG. 6.

In a particular aspect, the present invention provides 5-[4-[2-(N-methyl-N-(2-pyridyl)amino)ethoxy]benzyl]thiazolidine-2,4-dione mesylate salt (Form III), characterised by (i) an infrared spectrum containing peaks at about 1206, 603, 559, 545 cm$^{-1}$; and/or (ii) a Raman spectrum containing peaks at about 1205, 1179, 657, 557 cm$^{-1}$; and/or (iii) an X-ray powder diffraction (XRPD) pattern containing peaks at about 7.7, 14.8, 15.4, 16.9, 32.9 °2θ.

Depending on the solvent from which the Mesylate is recovered, the Mesylate may be obtained as a solvate, and such solvate is a favoured aspect of the invention.

In one favoured aspect, the Mesylate provides an infrared spectrum substantially in accordance with FIG. 7.

In one favoured aspect, the Mesylate provides a Raman spectrum substantially in accordance with FIG. 8.

In one favoured aspect, the Mesylate provides an X-Ray powder diffraction pattern (XRPD) substantially in accordance with Table 3 or FIG. 9.

In one particular aspect, the present invention provides 5-[4-[2-(N-methyl-N-(2-pyridyl)amino)ethoxy]benzyl]thiazolidine-2,4-dione mesylate salt (Form IV), characterised by (i) an infrared spectrum containing peaks at about 1549, 759, 600 cm$^{-1}$; and/or (ii) a Raman spectrum containing peaks at about 1338, 1183, 990, 552 cm$^{-1}$; and/or (iii) an X-ray powder diffraction (XRPD) pattern containing peaks at about 6.2, 11.9, 15.9, 19.8, 22.7 °2θ.

Depending on the solvent from which the Mesylate is recovered, the Mesylate may be obtained as a solvate, and such solvate is a favoured aspect of the invention.

In one favoured aspect, the Mesylate provides an infrared spectrum substantially in accordance with FIG. 10.

In one favoured aspect, the Mesylate provides a Raman spectrum substantially in accordance with FIG. 11.

In one favoured aspect, the Mesylate provides an X-Ray powder diffraction pattern (XRPD) substantially in accordance with Table 4 or FIG. 12.

In one favoured aspect, the Mesylate provides a Solid State $^{13}$C NMR spectrum substantially in accordance with FIG. 13.

In a further favoured aspect the Mesylate Form IV, provides a melting range in the range of 142 to 152° C., for example 148.9-150.3° C.

In a most preferred aspect, the invention provides 5-[4-[2-(N-methyl-N-(2-pyridyl)amino)ethoxy]benzyl]thiazolidine-2,4-dione, Mesylate salt Form IV, characterised in that it provides:

(i) an infrared spectrum substantially in accordance with FIG. 10; and (ii) a Raman spectrum substantially in accordance with FIG. 11; and (iii) an X-Ray powder diffraction pattern (XRPD) substantially in accordance with Table 4 or FIG. 12; and (iv) a Solid State $^{13}$C NMR spectrum substantially in accordance with FIG. 13.

The present invention encompasses the Mesylate or a solvate thereof isolated in pure form or when admixed with other materials.

Thus in one aspect there is provided the Mesylate or a solvate thereof in isolated form.

In a further aspect there is provided the Mesylate or a solvate thereof in pure form.

In yet a further aspect there is provided the Mesylate or a solvate thereof in crystalline form.

Also, the invention provides the Mesylate or solvate thereof in a solid pharmaceutically acceptable form, such as a solid dosage form, especially when adapted for oral administration.

Moreover, the invention also provides the Mesylate or solvate thereof in a pharmaceutically acceptable form, especially in bulk form, such form being particularly capable of being milled. The invention therefor also provides the Mesylate or solvate thereof in a milled form.

Furthermore, the invention provides the Mesylate or solvate thereof in a pharmaceutically acceptable form, especially in bulk form, such form having good flow properties, especially good bulk flow properties.

A suitable solvate is a a pharmaceutically acceptable solvate, such as a hydrate.

The invention also provides a process for preparing the Mesylate or a solvate thereof, characterised in that 5-[4-[2-(N-methyl-N-(2-pyridyl)amino)ethoxy]benzyl]thiazolidine-2,4-dione (Compound (I)), or a salt thereof, preferably dispersed or dissolved in a suitable solvent, is reacted with a suitable source of mesylate ion and thereafter, if required, a solvate of the resulting Mesylate is prepared; and the Mesylate or a solvate thereof is recovered.

Conveniently, the source of Mesylate ion is methanesulfonic acid. The methanesulfonic acid is preferably added as a liquid or in solution.

Suitable solvents include for example water, an ether such as tetrahydrofuran, a ketone such as acetone, a lower alcohol such as methanol, ethanol, or propan-2-ol, or a mixture of solvents. Other suitable solvents include toluene, acetonitrile, ethyl acetate or diethyl ether. As indicated, suitable solvents also include mixtures of the above-mentioned solvents.

An alternative source of Mesylate ion is provided by a suitably soluble base salt of methanesulfonic acid for example ammonium methanesulfonate, or the methanesulfonic acid salt of an amine, for example ethylamine or diethylamine.

The concentration of Compound (I) is preferably in the range 2 to 50% weight/volume, more preferably in the range 5 to 20%. The concentration of methanesulfonic acid solutions are preferably in the range of 5 to 150% weight/volume.

The reaction is usually carried out at ambient temperature or at an elevated temperature, for example 50-60° C. or at the reflux temperature of the solvent, although any convenient temperature that provides the required product may be employed.

Solvates, such as hydrates, of the Mesylate are prepared according to conventional procedures.

Recovery of the required compound generally comprises crystallisation from an appropriate solvent, conveniently the reaction solvent, usually assisted by cooling. For example, the Mesylate may be crystallised from an ether such as tetrahydrofuran, a nitrile such as acetonitrile, an ester such as ethyl acetate, or a lower alcohol such as propan-2-ol. An improved yield of the salt can be obtained by evaporation of some or all of the solvent or by crystallisation at elevated temperature followed by controlled cooling, optionally in stages. Careful control of precipitation temperature and seeding may be used to improve the reproducability of the product form.

Crystallisation can also be initiated by seeding with crystals of the Mesylate, especially Mesylate Form IV, or a solvate thereof but this is not essential, although it is preferred as mentioned for consistency of product form.

Compound (I) is prepared according to known procedures, such as those disclosed in EP-A-0 306 228 and WO 94/05659. The disclosures of EP-A-0 306 228 and WO 94/05659 are incorporated herein by reference.

Methanesulfonic acid is a commercially available compound.

When used herein the term "$T_{onset}$" is generally determined by Differential Scanning Calorimetry and has a meaning generally understood in the art, as for example expressed in Pharmaceutical Thermal Analysis, Techniques and Applications", Ford and Timmins, 1989 as "The temperature corresponding to the intersection of the pre-transition baseline with the extrapolated leading edge of the transition".

When used herein in respect of certain compounds the term "good flow properties" is suitably characterised by the said compound having a Hausner ratio of less than or equal to 1.5, especially of less than or equal to 1.25.

"Hausner ratio" is an art accepted term.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly provides the Mesylate or a solvate thereof for use as an active therapeutic substance.

More particularly, the present invention provides the Mesylate or a solvate thereof for use in the treatment and/or prophylaxis of diabetes mellitus, conditions associated with diabetes mellitus and certain complications thereof.

The Mesylate or a solvate thereof may be administered per se or, preferably, as a pharmaceutical composition also comprising a pharmaceutically acceptable carrier. Suitable methods for formulating the Mesylate or a solvate thereof are generally those disclosed for Compound (I) in the above mentioned publications.

Accordingly, the present invention also provides a pharmaceutical composition comprising the Mesylate or a solvate thereof and a pharmaceutically acceptable carrier therefor.

The Mesylate or a solvate thereof is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of the Mesylate or a solvate thereof to a human or non-human mammal in need thereof.

The compositions are formulated according to conventional methods, such as those disclosed in standard reference texts, for example the British and US Pharmacopoeias, Remington's Pharmaceutical Sciences (Mack Publishing Co.), Martindale The Complete Drug Reference (London, The Pharmaceutical Press) and Harry's Cosmeticology (Leonard Hill Books).

Conveniently, the active ingredient may be administered as a pharmaceutical composition hereinbefore defined, and this forms a particular aspect of the present invention.

In a further aspect the present invention provides the use of the Mesylate or a solvate thereof for the manufacture of a medicament for the treatment and/or prophylaxis of diabetes mellitus, conditions associated with diabetes mellitus and certain complications thereof.

In the treatment and/or prophylaxis of diabetes mellitus, conditions associated with diabetes mellitus and certain complications thereof, the Mesylate or a solvate thereof may be taken in amounts so as to provide Compound (I) in suitable doses, such as those disclosed in EP-A-0 306 228, WO 94/05659 or WO 98/55122.

No adverse toxicological effects are indicated in the above mentioned treatments for the compounds of the invention.

The following Preparations and Examples illustrate the invention but do not limit it in any way.

EXAMPLE 1

5-[4-[2-(N-methyl-N-(2-pyridyl)amino)ethoxy]benzyl]thiazolidine-2,4-dione methanesulfonate Form I A mixture of 5-[4-[2-(N-methyl-N-(2-pyridyl)amino) ethoxy]benzyl]thiazolidine-2,4-dione (4.7 g) and acetone (180 ml) was heated to reflux to give a clear solution. A solution of methanesulfonic acid (0.83 ml) in acetone (10 ml) was added and the mixture cooled to 21° C. After standing in a sealed vessel for 5 days at 21° C. crystals of 5-[4-[2-(N-methyl-N-(2-pyridyl)amino)ethoxy]benzyl]thiazolidine-2,4-dione methanesulfonate were collected by filtration.

EXAMPLE 2

5-[4-[2-(N-methyl-N-(2-pyridyl)amino)ethoxy]benzyl]thiazolidine-2,4-dione methanesulfonate Form I A mixture of 5-[4-[2-(N-methyl-N-(2-pyridyl)amino) ethoxy]benzyl]thiazolidine-2,4-dione (4.4 g) and toluene (35 ml) was heated to reflux until a clear solution was observed. The solution was cooled to 90° C. and seed crystals of 5-[4-[2-(N-methyl-N-(2-pyridyl)amino)ethoxy] benzyl]thiazolidine-2,4-dione methanesulfonate, prepared according to Example 1, were added followed immediately by methanesulfonic acid (0.8 ml). The mixture was cooled to 21° C. and sonicated for a period of 5 minutes and maintained at 21° C. until crystallisation was complete. The mixture was sonicated for a further 5 minutes and the product collected by filtration and dried under vacuum for 5 hours to give 5-[4-[2-(N-methyl-N-(2-pyridyl)amino) ethoxy]benzyl]thiazolidine-2,4-dione methanesulfonate (4.4 g).

1H-NMR (d6-DMSO): consistent with 5-[4-[2-(N-methyl-N-(2-pyridyl)amino)ethoxy]benzyl]thiazolidine-2,4-dione methanesulfonate.

Mpt: 119-125° C.

Characterising Data for the Mesylate Form I, Recorded for the Product of Example 2

The infrared absorption spectrum of a mineral oil dispersion of the product was obtained using a Nicolet 710 FT-IR spectrometer at 2 cm$^{-1}$ resolution (FIG. 1). Data were digitised at 1 cm$^{-1}$ intervals. Bands were observed at: 2925, 2853, 2770, 1747, 1697, 1636, 1610, 1545, 1515, 1466, 1413, 1377, 1330, 1312, 1286, 1260, 1241, 1214, 1180, 1150, 1091, 1069, 1040, 1003, 982, 933, 887, 828, 768, 715, 670, 617, 606, 549, 526, 509 cm$^{-1}$.

The infrared spectrum of the solid product was recorded using Perkin-Elmer Spectrum One FT-IR spectrometer fitted with a universal ATR accessory. Bands were observed at: 2958, 2771, 1747, 1696, 1636, 1610, 1545, 1515, 1467, 1438, 1413, 1385, 1312, 1286, 1241, 1214, 1180, 1149, 1091, 1069, 1039, 1003, 982, 933, 887, 827, 767, 736, 715, 669 cm$^{-1}$.

The Raman spectrum of the product (FIG. 2) was recorded with the sample in a glass vial using a Perkin-Elmer 2000R FT-Raman spectrometer, at 4 cm-1 resolution with excitation from a Nd:YAG laser (1064 nm) with a power output of 400 mW. Bands were observed at: 3105, 3070, 3015, 2937, 1747, 1613, 1547, 1468, 1448, 1425, 1386, 1332, 1302, 1287, 1264, 1248, 1212, 1186, 1157, 1037, 982, 955, 934, 887, 849, 825, 774, 739, 721, 671, 638, 607, 548, 510, 475, 442, 421, 400, 383, 341, 299, 216 cm$^{-1}$.

The X-Ray Powder Diffractogram pattern of the product (FIG. 3) was recorded using the following acquisition conditions: Tube anode: Cu, Generator tension: 40 kV, Generator current: 40 mA, Start angle: 2.0 °2θ, End angle: 35.0 °2θ, Step size: 0.02 °2θ, Time per step: 2.5 seconds. Characteristic XRPD angles and relative intensities are recorded in Table 1.

TABLE 1

| Angle 2-Theta° | Rel. Intensity % |
|---|---|
| 4.6 | 2.4 |
| 9.3 | 16.8 |
| 11.4 | 1.8 |
| 14.0 | 3.3 |
| 16.8 | 7.0 |
| 17.4 | 11.6 |
| 18.1 | 24.8 |
| 18.5 | 50.7 |
| 18.8 | 33.7 |
| 19.2 | 28.0 |
| 19.6 | 10.3 |
| 20.0 | 11.1 |
| 20.7 | 100.0 |
| 21.0 | 41.9 |
| 21.8 | 35.6 |
| 22.5 | 32.7 |
| 23.2 | 36.2 |
| 23.5 | 32.0 |
| 24.0 | 13.9 |
| 24.4 | 11.6 |
| 24.7 | 10.7 |

TABLE 1-continued

| Angle 2-Theta° | Rel. Intensity % |
|---|---|
| 25.6 | 31.6 |
| 26.3 | 15.5 |
| 26.7 | 22.0 |
| 27.2 | 17.9 |
| 27.6 | 8.6 |
| 28.5 | 17.5 |
| 29.2 | 24.8 |
| 29.8 | 21.2 |
| 30.3 | 16.4 |
| 31.2 | 11.2 |
| 32.4 | 14.1 |
| 32.8 | 18.5 |
| 33.3 | 11.0 |
| 34.4 | 11.7 |

Properties of the Mesylate Form I Recorded for the Product of Example 1

Solubility of the Mesylate

The solubility of the material was determined by adding water in aliquots from 0.1 to 1 ml to approximately 15 mg of drug substance until the powder had dissolved Solubility: >100 mg/ml.

EXAMPLE 3

5-[4-[2-(N-methyl-N-(2-pyridyl)amino)ethoxy]benzyl]thiazolidine-2,4-dione methanesulfonate Form II A mixture of 5-[4-[2-(N-methyl-N-(2-pyridyl)amino)ethoxy]benzyl]thiazolidine-2,4-dione (5.0 g) and propan-2-ol (70 ml) was warmed to 70° C. with stirring under a nitrogen atmosphere. A solution of methanesulfonic acid (1.5 g) in propan-2-ol (5 ml) was added to the stirred mixture and the temperature raised to 75° C. Stirring was continued for 30 minutes to give a clear solution. The solution was cooled to 30° C. over a period of one hour and seeded with the product of Example 2. The mixture was warmed to 55° C. and stirred at this temperature for 90 minutes before cooling to 21° C. The product was collected by filtration, washed with propan-2-ol (20 ml) and dried under vacuum for 5 hours to give 5-[4-[2-(N-methyl-N-(2-pyridyl)amino)ethoxy]benzyl]thiazolidine-2,4-dione methanesulfonate as a white crystalline solid (5.95 g).

1H-NMR (d6-DMSO): consistent with 5-[4-[2-(N-methyl-N-(2-pyridyl)amino)ethoxy]benzyl]thiazolidine-2,4-dione methanesulfonate Mpt: 115-120° C.

Characterising Data Recorded for the Product of Example 3

The infrared absorption spectrum of a mineral oil dispersion of the product was obtained using a Nicolet 710 Fr-IR spectrometer at 2 cm$^{-1}$ resolution (FIG. 4). Data were digitised at 1 cm$^{-1}$ intervals. Bands were observed at: 1749, 1695, 1636, 1610, 1544, 1512, 1413, 1331, 1311, 1286, 1260, 1224, 1179, 1149, 1091, 1068, 1039, 1003, 994, 934, 883, 825, 769, 740, 716, 674, 617, 609, 592, 550, 524 and 509 cm$^{-1}$.

The infrared spectrum of the solid product was recorded using Perkin-Elmer Spectrum One FT-IR spectrometer fitted with a universal ATR accessory. Bands were observed at: 2768, 1748, 1686, 1636, 1609, 1545, 1512, 1477, 1414, 1312, 1214, 1179, 1148, 1092, 1068, 1039, 1004, 934, 883, 826, 768, 716, 673 cm$^{-1}$.

The Raman spectrum of the product (FIG. 5) was recorded with the sample in a glass vial using a Perkin-Elmer 2000R FT-Raman spectrometer, at 4 cm$^{-1}$ resolution with excitation from a Nd:YAG laser (1064 nm) with a power output of 400 mW. Bands were observed at: 3104, 3068, 3016, 2938, 1749, 1611, 1582, 1547, 1467, 1448, 1424, 1387, 1331, 1300, 1287, 1264, 1245, 1212, 1185, 1156, 1067, 1037, 983, 955, 883, 850, 824, 777, 759, 740, 721, 674, 638, 609, 549, 533, 508, 476, 444, 401, 342, 299, 215 cm$^{-1}$.

The X-Ray Powder Diffractogram pattern of the product (FIG. 6) was recorded using the following acquisition conditions: Tube anode: Cu, Generator tension: 40 kV, Generator current: 40 mA, Start angle: 2.0 °2θ, End angle: 35.0 °2θ, Step size: 0.02 °2θ, Time per step: 2.5 seconds. Characteristic XRPD angles and relative intensities are recorded in Table 2.

TABLE 2

| Angle 2-Theta° | Rel. Intensity % |
|---|---|
| 4.6 | 1.2 |
| 9.2 | 14.2 |
| 11.3 | 2.7 |
| 13.8 | 3.6 |
| 17.1 | 5 |
| 18.0 | 23.2 |
| 18.4 | 24.2 |
| 18.7 | 34.1 |
| 19.3 | 45.8 |
| 20.2 | 11.7 |
| 21.0 | 100 |
| 21.4 | 22.9 |
| 22.2 | 10.2 |
| 22.6 | 27.3 |
| 23.2 | 24 |
| 23.5 | 22.8 |
| 24.0 | 10.4 |
| 24.4 | 12.2 |
| 25.1 | 10.4 |
| 25.5 | 23.5 |
| 25.9 | 12.1 |
| 26.3 | 9.4 |
| 26.8 | 12.2 |
| 27.2 | 17.4 |
| 27.5 | 8.4 |
| 28.0 | 11.1 |
| 28.8 | 15.4 |
| 29.0 | 16.2 |
| 29.5 | 15.9 |
| 30.1 | 7.3 |
| 30.4 | 7.1 |
| 31.1 | 8.2 |
| 32.4 | 8.6 |
| 32.7 | 12.2 |
| 33.2 | 10.1 |
| 34.0 | 9.6 |
| 34.4 | 9.8 |

Properties of the Mesylate Form II Recorded for the Product of Example 3

Solubility of the Mesylate

The solubility of the material was determined by adding water in aliquots from 0.5 to 1 ml to approximately 100 mg of drug substance until the powder had dissolved Solubility: >100 mg/ml.

EXAMPLE 4

5-[4-[2-(N-methyl-N-(2-pyridyl)amino)ethoxy]benzyl]thiazolidine-2,4-dione methanesulfonate Form III 5-[4-[2-(N-methyl-N-(2-pyridyl)amino)ethoxy]benzyl]thiazolidine-2,4-dione (15 g) in acetone (230 ml) was stirred and heated to reflux for 30 minutes at which point a clear solution was observed. Methanesulfonic acid (4.0 g) was added and the mixture was stirred at reflux for 5 minutes, then cooled to 40° C. and stirred until crystallisation was observed. After cooling to 21° C. the product was collected by filtration and dried under vacuum at 21° C. to provide 5-[4-[2-(N-methyl-N-(2-pyridyl)amino)ethoxy]benzyl]thiazolidine-2,4-dione methanesulfonate (17.3 g) as a white crystalline solid.

1H-NMR (d6-DMSO): consistent with 5-[4-[2-(N-methyl-N-(2-pyridyl)amino)ethoxy]benzyl]thiazolidine-2,4-dione methanesulfonate.

Mpt: 113-120° C.

EXAMPLE 5

5-[4-[2-(N-methyl-N-(2-pyridyl)amino)ethoxy]benzyl]thiazolidine-2,4-dione methanesulfonate Form III Methanesulfonic acid (1.69 g) was added to a suspension of 5-[4-[2-(N-methyl-N-(2-pyridyl)amino)ethoxy]benzyl]thiazolidine-2,4-dione (6.0 g) and ethanol (50 ml) and the mixture was stirred and heated to give a clear solution. Diethyl ether (50 ml) was added and the mixture was heated to reflux and then cooled to 21° C. over a period of 1 hour. The product was collected by filtration, washed with diethyl ether (50 ml) and dried under vacuum for 2 hours at 21° C. to give 5-[4-[2-(N-methyl-N-(2-pyridyl)amino)ethoxy]benzyl]thiazolidine-2,4-dione methanesulfonate (6.40 g) as a white crystalline solid.

Characterising Data for the Mesylate Form III Recorded for the Product of Example 4

The infrared absorption spectrum of a mineral oil dispersion of the product was obtained using a Nicolet 710 FT-IR spectrometer at 2 cm$^{-1}$ resolution (FIG. 7). Data were digitised at 1 cm$^{-1}$ intervals. Bands were observed at: 3113, 2926, 2853, 2761, 1747, 1693, 1647, 1610, 1546, 1511, 1466, 1418, 1332, 1304, 1260, 1238, 1206, 1185, 1157, 1097, 1040, 1027, 1010, 983, 902, 819, 773, 739, 722, 713, 655, 618, 603, 559, 545, 521, 507 cm$^{-1}$.

The infrared spectrum of the solid product was recorded using Perkin-Elmer Spectrum One FT-IR spectrometer fitted with a universal ATR accessory. Bands were observed at: 2918, 2754, 1747, 1692, 1646, 1610, 1546, 1511, 1468, 1439, 1416, 1332, 1303, 1258, 1237, 1205, 1182, 1155, 1039, 982, 902, 819, 772, 739, 712, 668, 654 cm$^{-1}$.

The Raman spectrum of the product (FIG. 8) was recorded with the sample in a glass vial using a Perkin-Elmer 2000R FT-Raman spectrometer, at 4 cm$^{-1}$ resolution with excitation from a Nd:YAG laser (1064 nm) with a power output of 400 mW. Bands were observed at: 3099, 3008, 2935, 1747, 1610, 1546, 1441, 1386, 1332, 1266, 1205, 1179, 1079, 1042, 985, 920, 820, 776, 740, 657, 636, 618, 603, 557, 544, 522, 469, 407, 392, 339, 226 cm$^{-1}$.

The X-Ray Powder Diffractogram pattern of the product (FIG. 9) was recorded using the following acquisition conditions: Tube anode: Cu, Generator tension: 40 kV, Generator current: 40 mA, Start angle: 2.0 °2θ, End angle: 35.0 °2θ, Step size: 0.02 °2θ, Time per step: 2.5 seconds. Characteristic XRPD angles and relative intensities are recorded in Table 3.

TABLE 3

| Angle 2-Theta° | Rel. Intensity % |
|---|---|
| 4.5 | 9.4 |
| 7.7 | 16.1 |
| 10.9 | 21.4 |
| 12.5 | 4.7 |
| 13.3 | 38.6 |
| 14.6 | 6.2 |
| 14.8 | 7.9 |
| 15.4 | 9 |
| 16.9 | 100 |
| 17.2 | 57 |
| 17.9 | 46.9 |
| 18.2 | 17.8 |
| 18.7 | 10.3 |
| 18.9 | 8.6 |
| 20.4 | 8.2 |
| 20.9 | 9.3 |
| 22.1 | 18.9 |
| 22.5 | 34 |
| 22.7 | 42.6 |
| 23.2 | 38.3 |
| 23.5 | 36.1 |
| 24.7 | 28.3 |
| 25.6 | 16.2 |
| 25.9 | 24.6 |
| 26.2 | 36.3 |
| 26.8 | 15.1 |
| 27.8 | 16.6 |
| 29.1 | 16.8 |
| 29.8 | 16.6 |
| 30.5 | 12.2 |
| 31.1 | 9.1 |
| 31.7 | 11 |
| 32.0 | 14 |
| 32.9 | 11.4 |
| 34.0 | 9 |
| 34.5 | 13.2 |

Properties of the Mesylate Form III Recorded for the Product of Example 4

Solubility of the Mesylate

The solubility of the material was determined by adding water in aliquots from 0.5 to 1 ml to approximately 100 mg of drug substance until the powder had dissolved Solubility: >100 mg/ml.

EXAMPLE 6

5-[4-[2-(N-methyl-N-(2-pyridyl)amino)ethoxy]benzyl]thiazolidine-2,4-dione methanesulfonate Form IV A solution of 5-[4-[2-(N-methyl-N-(2-pyridyl)amino)ethoxy]benzyl]thiazolidine-2,4-dione (3.0 g) in tetrahydrofuran (30 ml) was stirred and heated to 50° C. Methanesulfonic acid (0.54 ml) was added and the mixture heated to reflux and seeded with the product of Example 2. The stirred mixture was cooled to 21° C. over a period of approximately 1 hour and the product was collected by filtration, and dried under vacuum to give 5-[4-[2-(N-methyl-N-(2-pyridyl)amino)ethoxy]benzyl]thiazolidine-2,4-dione methanesulfonate as a white crystalline solid (3.32 g).

1H-NMR (d6-DMSO): consistent with 5-[4-[2-(N-methyl-N-(2-pyridyl)amino)ethoxy]benzyl]thiazolidine-2,4-dione methanesulfonate.

Melting Point: 145.8° C.

EXAMPLE 7

5-[4-[2-(N-methyl-N-(2-pyridyl)amino)ethoxy]benzyl]thiazolidine-2,4-dione methanesulfonate Form IV Methanesulfonic acid (2.3 ml) was added to a stirred suspension of 5-[4-[2-(N-methyl-N-(2-pyridyl)amino)ethoxy]benzyl]thiazolidine-2,4-dione (12.0 g) in ethanol (100 ml) at 21° C. The reaction mixture was heated to reflux for 30 minutes then cooled to 21° C. Diethyl ether (100 ml) was added and the reaction heated to reflux for 1 hour, then cooled to 21° C. The reaction was heated to reflux, diethyl ether (50 ml) was added and stirred for 30 minutes, cooled to 21° C. over approximately 1 hour, then stirred for 16 hours at 21° C. The product was collected by filtration and dried under vacuum to afford 5-[4-[2-(N-methyl-N-(2-pyridyl)amino)ethoxy]benzyl]thiazolidine-2,4-dione methanesulfonate (14.8 g) as a white crystalline solid.

EXAMPLE 8

5-[4-[2-(N-methyl-N-(2-pyridyl)amino)ethoxy]benzyl]thiazolidine-2,4-dione methanesulfonate Form IV A solution of methanesulfonic acid (0.55 g) in tetrahydrofuran (10 ml) was added to a stirred solution of 5-[4-[2-(N-methyl-N-(2-pyridyl)amino)ethoxy]benzyl] thiazolidine-2,4-dione (2.50 g) in tetrahydrofuran (50 ml) at 21° C. The mixture was stirred for 5 minutes and then cooled to 4° C. for a period of 16 hours. The product was collected by filtration, washed with tetrahydrofuran (10 ml) and dried under vacuum at 21° C. for 3 hours to give 5-[4-[2-(N-methyl-N-(2-pyridyl)amino)ethoxy]benzyl]thiazolidine-2,4-dione methanesulfonate (2.95 g) as a white crystalline solid.

EXAMPLE 9

5-[4-[2-(N-methyl-N-(2-pyridyl)amino)ethoxy]benzyl]thiazolidine-2,4-dione methanesulfonate Form IV A suspension of 5-[4-[2-(N-methyl-N-(2-pyridyl)amino)ethoxy]benzyl] thiazolidine-2,4-dione (3.0 g) in acetonitrile (60 ml) was heated to 60° C. Methanesulfonic acid (0.54 ml) was added and the mixture stirred at 60° C. to give a clear solution. After cooling to 21° C. the solvent was evaporated under reduced pressure, propan-2-ol (20 ml) added to the residue and the mixture stirred at 21° C. to give a white suspension. The product was collected by filtration, washed with propan-2-ol and dried under vacuum for 5 hours to give 5-[4-[2-(N-methyl-N-(2-pyridyl)amino)ethoxy]benzyl]thiazolidine-2,4-dione methanesulfonate (3.37 g) as a white crystalline solid.

EXAMPLE 10

5-[4-[2-(N-methyl-N-(2-pyridyl)amino)ethoxy]benzyl]thiazolidine-2,4-dione methanesulfonate Form IV Methanesulfonic acid (0.54 ml) was added to a mixture of 5-[4-[2-(N-methyl-N-(2-pyridyl)amino)ethoxy]benzyl]thiazolidine-2,4-dione (3.0 g) and ethyl acetate (60 ml) and the reaction mixture stirred and heated to reflux to give a suspension. After cooling to 21° C. the product was collected by filtration, washed with ethyl acetate (10 ml) and dried under vacuum for 16 hours to give 5-[4-[2-(N-methyl-N-(2-pyridyl)amino)ethoxy]benzyl]thiazolidine-2,4-dione methanesulfonate (3.73 g) as a white crystalline solid.

EXAMPLE 11

5-[4-[2-(N-methyl-N-(2-pyridyl)amino)ethoxy]benzyl]thiazolidine-2,4-dione methanesulfonate Form IV A mixture of 5-[4-[2-(N-methyl-N-(2-pyridyl)amino)ethoxy]benzyl]thiazolidine-2,4-dione (12.0 g) and propan-2-ol (360 ml) was stirred and heated to reflux for 10 minutes at which point a clear solution was observed. Methanesulfonic acid (4.04 ml) was added and the stirred reaction mixture cooled to 75° C., seeded with the product of Example 6 and then cooled to 21° C. over a period of approximately 1 hour. The solid was collected by filtration, washed with propan-2-ol (50 ml) and dried under vacuum for 16 hours to give 5-[4-[2-(N-methyl-N-(2-pyridyl)amino)ethoxy]benzyl]thiazolidine-2,4-dione methanesulfonate (13.8 g) as a white crystalline solid.

Characterising Data for the Mesylate Form IV Recorded for the Product of Example 6

The infrared absorption spectrum of a mineral oil dispersion of the product was obtained using a Nicolet 710 FT-IR spectrometer at 2 cm$^{-1}$ resolution (FIG. 10). Data were digitised at 1 cm$^{-1}$ intervals. Bands were observed at: 3115, 2926, 2854, 2771, 1747, 1702, 1646, 1617, 1586, 1549, 1512, 1459, 1423, 1377, 1336, 1314, 1303, 1243, 1155, 1109, 1040, 1008, 911, 830, 816, 775, 759, 736, 714, 662, 620, 600, 552, 531, 505 cm$^{-1}$.

The infrared spectrum of the solid product was recorded using Perkin-Elmer Spectrum One FT-IR spectrometer fitted with a universal ATR accessory. Bands were observed at: 2771, 1747, 1698, 1646, 1613, 1587, 1550, 1512, 1478, 1451, 1422, 1388, 1335, 1314, 1239, 1153, 1110, 1032, 1008, 963, 911, 829, 816, 774, 758, 736, 713, 660 cm$^{-1}$.

The Raman spectrum of the product (FIG. 11) was recorded with the sample in a glass vial using a Perkin-Elmer 2000R FT-Raman spectrometer, at 4 cm-1 resolution with excitation from a Nd:YAG laser (1064 nm) with a power output of 400 mW. Bands were observed at: 3107, 3063, 3007, 2933, 1748, 1700, 1613, 1587, 1549, 1452, 1422, 1389, 1338, 1313, 1289, 1264, 1248, 1209, 1183, 1150, 1112, 1084, 1042, 1010, 990, 963, 916, 840, 776, 741, 720, 665, 636, 620, 601, 552, 529, 498, 469, 430, 412, 399, 389, 344, 337, 298, 263, 228 cm$^{-1}$.

The X-Ray Powder Diffractogram pattern of the product (FIG. 12) was recorded using the following acquisition conditions: Tube anode: Cu, Generator tension: 40 kV, Generator current: 40 mA, Start angle: 2.0 °2θ, End angle: 35.0 °2θ, Step size: 0.02 °2θ, Time per step: 2.5 seconds. Characteristic XRPD angles and relative intensities are recorded in Table 4.

TABLE 4

| Angle 2-Theta° | Rel. Intensity % |
|---|---|
| 6.2 | 3.2 |
| 9.2 | 12.1 |
| 10.8 | 10.9 |
| 11.4 | 4.2 |
| 11.9 | 9.7 |
| 12.4 | 8.2 |
| 13.3 | 34 |
| 14.5 | 4.7 |
| 15.0 | 2.5 |
| 15.9 | 7.9 |
| 16.8 | 100 |
| 17.6 | 2.3 |
| 18.4 | 11.3 |
| 18.6 | 43.8 |
| 19.0 | 3.5 |
| 19.8 | 12.1 |
| 20.3 | 7.5 |
| 21.2 | 32.2 |
| 21.6 | 33.6 |
| 21.9 | 21.1 |
| 22.1 | 14 |
| 22.4 | 30.1 |
| 22.7 | 80.2 |
| 23.0 | 24.6 |
| 23.9 | 4.7 |
| 24.5 | 8.8 |
| 25.0 | 4.8 |
| 25.6 | 7.5 |
| 26.1 | 8.9 |
| 26.6 | 19.1 |
| 27.1 | 7.1 |
| 27.6 | 7.8 |
| 28.0 | 21 |
| 29.3 | 5.3 |
| 29.9 | 14.6 |
| 30.3 | 5.9 |
| 31.4 | 12.6 |
| 31.6 | 6.5 |
| 32.1 | 11.2 |
| 33.1 | 10 |
| 33.4 | 3 |

The solid-state NMR spectrum of the product (FIG. 13) was recorded on a Bruker AMX360 instrument operating at 90.55 MHz: The solid was packed into a 4 mm zirconia MAS rotor fitted with a Kel-F cap and rotor spun at ca.10 kHz. The $^{13}$C MAS spectrum was acquired by cross-polarisation from Hartmann-Hahn matched protons (CP contact time 3 ms, repetition time 15 s) and protons were decoupled during acquisition using a two-pulse phase modulated (TPPM) composite sequence. Chemical shifts were externally referenced to the carboxylate signal of glycine at 176.4 ppm relative to TMS and were observed at: 37.4, 40.1, 49.9, 55.9, 67.8, 111.2, 115.6, 118.9, 130.7, 131.4, 134.3, 140.3, 141.5, 153.0, 157.2, 157.7, 171.8, 176.7 ppm.

Properties of the Mesylate Form IV

Solid State Stability of the Mesylate Form IV Recorded for the Product of Example 11

The solid state stability of the drug substance was determined by storing approximately 1.0 g of the material in a glass bottle at a) 40° C./75% Relative Humidity (RH), open exposure, for 1 month and b) at 50° C., closed, for 1 month. The material was assayed by HPLC for final content and degradation products in both cases.

a) 40° C./75% RH: No significant degradation observed (HPLC assay 98% initial).

b) 50° C.: No significant degradation observed (HPLC assay 100% initial).

Solubility of the Mesylate Form IV recorded for the product of Example 11

The solubility of the material was determined by adding water in aliquots from 1 to 1000 ml to approximately 100 mg of drug substance until the powder had dissolved. The visual solubility was confirmed by an HPLC assay of a saturated solution.

Solubility: >100 mg/ml.

Flow Properties of the Mesylate Form IV Recorded for the Product of Example 11

The ratio between the bulk density and the tapped bulk density (Hausner Ratio) of the Mesylate was determined using standard methods ("Pharmaceutics—The Science of Dosage Form Design", editor M. Aulton, 1988, published by:Churchill Livingstone). Hausner Ratio: 1.2

$T_{onset}$ of the Mesylate Form IV Recorded for the Product of Example 11

The $T_{onset}$ of the drug substance was determined by Differential Scanning Calorimetry using a Perkin-Elmer DSC7 apparatus.

$T_{onset}$ (10° C./minute, closed pan): 147° C.

Melting Range of the Mesylate Form IV Recorded for the Product of Example 7

The melting range of the Mesylate was determined according to the method described in the U.S. Pharmacopoeia, USP 23, 1995, <741> "Melting range or temperature, Procedure for Class Ia", using a Buchi 545 melting point instrument.

Melting range: 148.9-150.3° C.

The invention claimed is:

1. A crystalline 5-[4-[2-(N-methyl-N-(2-pyridyl)amino)ethoxy]benzyl]thiazolidine-2,4-dione mesylate which provides at least one of:
    (i) an infra red spectrum containing peaks at about 1549, 759, 600 cm$^{-1}$;
    (ii) a Raman spectrum containing peaks at about 1338, 1183, 990, 552 cm$^{-1}$; and
    (iii) an X-ray powder diffraction pattern containing peaks at about 6.2, 11.9, 15.9, 19.8, 22.7 °2θ.

2. A crystalline 5-[4-[2-(N-methyl-N-(2-pyridyl)amino)ethoxy]benzyl]thiazolidine-2,4-dione mesylate which provides at least one of:
    (i) in a mineral oil dispersion, an infra red spectrum substantially in accordance with FIG. 10;
    (ii) a Raman spectrum substantially in accordance with FIG. 11;
    (iii) an X-ray powder diffraction pattern substantially in accordance with FIG. 12; and
    (iv) a solid state $^{13}$C NMR spectrum substantially in accordance with FIG. 13.

3. A crystalline 5-[4-[2-(N-methyl-N-(2-pyridyl)amino)ethoxy]benzyl]thiazolidine-2,4-dione mesylate which provides an FT infra red spectrum containing bands at 2771, 1747, 1698, 1646, 1613, 1587, 1550, 1512, 1478, 1451, 1422, 1388, 1335, 1314, 1239, 1153, 1110, 1032, 1008, 963, 911, 829, 816, 774, 758, 736, 713, 660 cm$^{-1}$.

* * * * *